Figure 1:
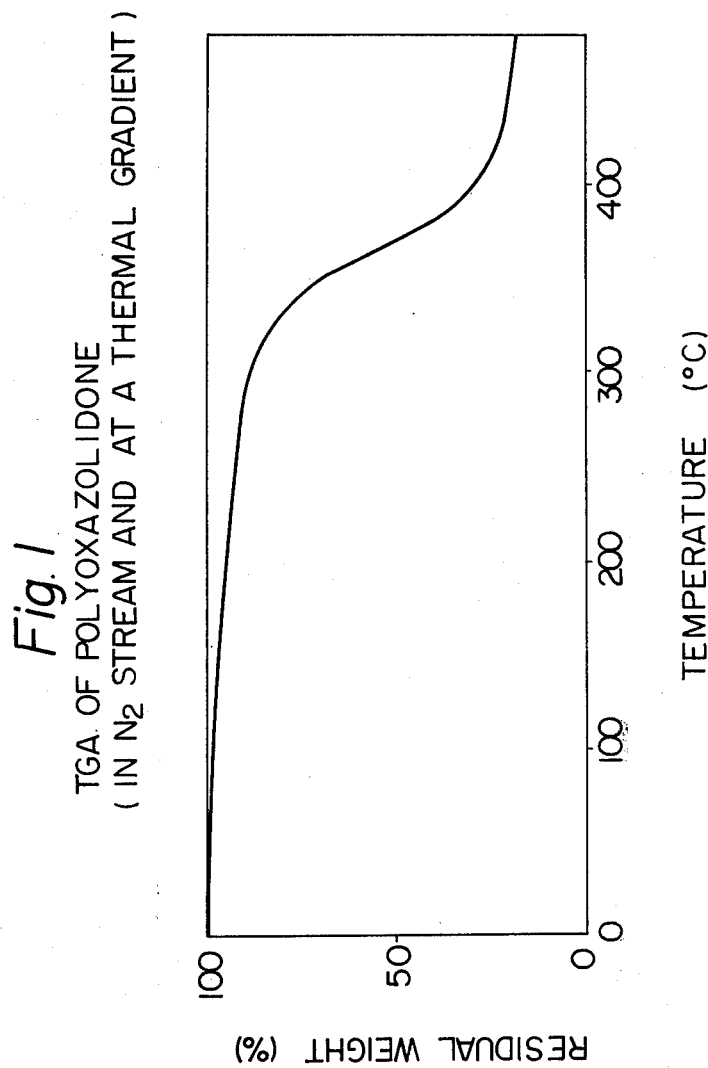

United States Patent [19]

Ashida

[11] 4,022,721
[45] May 10, 1977

[54] PROCESS FOR PRODUCING COMPOUNDS HAVING AN OXAZOLIDONE RING USING A COMPLEX OF ALUMINUM HALIDE CATALYST

[75] Inventor: Kaneyoshi Ashida, Chofu, Japan

[73] Assignee: Mitsubishi Chemical Industries Ltd., Tokyo, Japan

[22] Filed: Sept. 15, 1975

[21] Appl. No.: 613,175

[30] Foreign Application Priority Data

Sept. 26, 1974 Japan ............................ 49-110727
Sept. 27, 1974 Japan ............................ 49-111173
Sept. 27, 1974 Japan ............................ 49-111174

[52] U.S. Cl. .................... 260/2.5 AC; 260/2.5 AB; 260/2.5 AW; 260/47 CB; 260/47 EP; 260/75 NB; 260/75 NC; 260/77.5 AB; 260/77.5 AC; 260/77.5 R; 260/307 C
[51] Int. Cl.² ................ C08G 18/00; C08G 18/16; C08G/18/18
[58] Field of Search ................ 260/2.5 AB, 2.5 AC, 260/77.5 AB, 77.5 AC, 47 CB, 47 EP, 307 C, 77.5 R, 2.5 AW, 75 NB, 75 NC

[56] References Cited

UNITED STATES PATENTS

| 2,977,369 | 3/1961 | Dixon et al. | 260/307 C |
|---|---|---|---|
| 3,687,897 | 8/1972 | Clarke | 260/77.5 AB |
| 3,694,406 | 9/1972 | D'Alelio | 260/77.5 NC |
| 3,702,839 | 11/1972 | Glasgow et al. | 260/77.5 AB |
| 3,721,650 | 3/1973 | D'Alelio | 260/77.5 R |
| 3,737,406 | 6/1973 | D'Alelio | 260/77.5 AB |
| 3,817,938 | 6/1974 | Ashida et al. | 260/77.5 R |
| 3,905,945 | 9/1975 | Iseda et al. | 260/77.5 R |

OTHER PUBLICATIONS

Journal of Polymer Science, Part 4-1, vol. 5, (1967), pp. 1481–1485, Sandler.

*Primary Examiner*—Eugene C. Rzucidlo
*Attorney, Agent, or Firm*—Bierman & Bierman

[57] ABSTRACT

A process is disclosed for producing a compound, having an oxazolidone ring, by reacting an isocyanate compound and an epoxy compound wherein said reaction is catalytically promoted in the presence of an effective amount of a complex of a Lewis acid, especially a certain metal halide, with at least one Lewis base select from an ether, a thioether, an amine, a lactam, an amide, or a certain phosphorus or sulfur compound.

27 Claims, 2 Drawing Figures

TGA OF POLYOXAZOLIDONE
(IN N₂ STREAM AND AT A THERMAL GRADIENT)

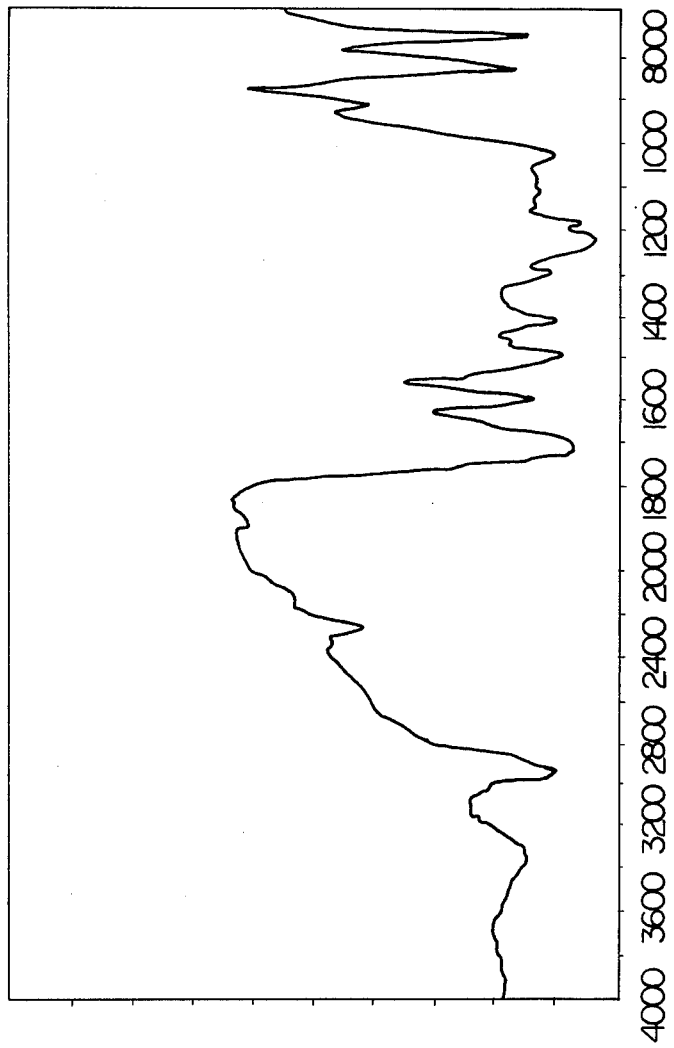

PROCESS FOR PRODUCING COMPOUNDS HAVING AN OXAZOLIDONE RING USING A COMPLEX OF ALUMINUM HALIDE CATALYST

This invention relates to a process for producing a compound containing an oxazolidone ring and, more particularly to a process in which an isocyanate compound and an epoxy compound are reacted in the presence of a novel catalyst to produce an oxazolidone compound. The formation of an oxazolidone compound is represented by the following reaction formula:

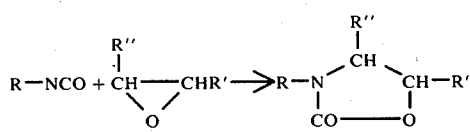

wherein R represents an isocyanate residue, R' represents an epoxy residue and R'' represents hydrogen or an epoxy residue.

Examples of known catalyst which promote the formation of an oxazolidone compound are, for example, a quaternary ammonium halide (U.S. Pat. No. 3,313,747, a Lewis acid, such as zinc bromide, zinc chloride and iron chloride [Sandler, J. Polymer Science A-1, Vol. 5, 1481 (1967)], lithium chloride [K. Gulbins et al., Chem. Ber. 93, 1975 (1960)] and n-butoxy lithium [R. R. Dileone, J. Polymer Science A-1, Vol. 8, 609 (1970) ].

These catalysts are hardly soluble in isocyanate compounds, epoxy compounds and conventional organic solvent which are employed for the production of an oxazolidone compound. Therefore, the reaction will proceed in a heterogeneous system resulting in a slow reaction rate a high reaction temperature and a long reaction time additionally, undesirable side reaction are known to occur.

I have found that a certain soluble complex shows excellent catalytic activity and is suitable for the production of an oxazolidone compound, and this invention is accomplished on the basis of this knowledge. The complex is derived from a Lewis acid as an electron acceptor and at least one Lewis base as an electron donor selected from the group consisting of an ether, a thioether, an amine, a lactam, an N-alkyl lactam, an amide, an N-alkyl amide, a phosphorus compound represented by general formulae (1) and (2) and a sulfur compound represented by general formula (3):

1. $R^1_3P$, wherein each $R^1$ may be the same or different and represents hydrogen and hydrocarbon with the proviso that each $R^1$ may not be hydrogen at the same time, and when two or more are hydrocarbon they may be combined to form alkylene,
2. $R^2_3PO$, wherein each $R^2$ may be the same or different and represents alkyl, cycloalkyl, aryl, alkoxy and acyl which may be substituted by alkoxy, acyloxy and halogen, and
3. $R^3_2SO$, wherein each $R^3$ may be the same or different and represents hydrocarbon.

The Lewis acid may be any of a wide variety of metal halides disclosed in, for example, "Encyclopedia of Chemical Technology" by R. E. Kirk and D. F. Othmer, Vol. 10, p. 159 and "Vinyl Polymerization" by G. E. Ham, Part II, p. 258 and examples of such metal include, for example, Be, Zn, Cd, B, Al, Ga, Ti, Zr, Sb, Sn, Bi, Fe, Co, and V. The preferred metals are those having an atomic number of from 13 to 48 and belonging to Groups IIB and IIIA. The more preferred iron family of the Periodic Table and metals are Zn, Al and Fe, especially Al. (The Periodic Table referred to is described in "The Handbook of Chemistry and Physics" edited by Charles D. Hodgeman and published by Chemical Rubber Publishing Co., Vol. 33, pages 342 to 343.)

Halides of these metals include fluorine, chlorine, bromine iodine, with chlorine and bromine being the most preferred. Thus, the preferred metal halides are, for example, $AlCl_3$, $AlBr_3$, $FeCl_3$, $ZnCl_2$ and $ZnBr_2$.

A wide range of ethers and thioethers are operable in the present process but it is preferred to use those which are liquid at ambient temperature.

In general, an ether or thioether containing hydrocarbon of 1 to 8 carbon atoms is used, for example, an aliphatic ether such as diethyl ether, di-isopropyl ether and dibutyl ether; a cycloaliphatic ether such as tetrahydrofuran, dioxane, pyran and tetrahydropyran; an aromatic ether such as diphenyl ether, anisole and phenylethyl ether; an aliphatic thioether such as dimethyl sulfide, diethyl sulfide, di-isopropyl sulfide, dibutyl sulfide and divinyl sulfide; and an aromatic thioether such as diphenyl sulfide and dibenzyl sulfide of these ethers, aliphatic and cycloaliphatic ethers are preferred.

Among the complexes of a Lewis acid with an ether, it should be noted that the catalytic activity of a complex of boron halide and an ether, for example, $BF_3 \cdot O(C_2H_5)_2$ is significantly inferior to other complexes.

The amine which forms the complex with a Lewis acid may be selected from a wide variety of primary, secondary and tertiary amines. The amine residue thereof may be aliphatic, cycloaliphatic, aromatic or heterocyclic, whichever contains one or more substituents unreactive with the isocyanate group. In general, an amine containing 1 to 18 carbon atoms is preferred.

Examples of the primary amine include, for example, an aliphatic amine such as ethylamine, n-propylamine, isopropylamine, n-butylamine, n-hexylamine, dodecylamine, tetradecylamine, allylamine, ethylenediamine, propylenediamine and hexamethylenediamine; an aromatic amine such as aniline, toluidine, m-phenylenediamine, xylenediamine; benzylamine and naphthylamine, and a cycloaliphatic amine such as cyclohexylamine and 4-methyl cyclohexylamine.

Examples of the secondary amine include, for example, an aliphatic amine such as diethylamine and di-n-butylamine; an aromatic amine such as N-methylaniline and N-ethyltoluidine; a cycloaliphatic amine such as N-methyl cyclohexylamine, N-ethyl cyclohexylamine and dicyclohexylamine; and a nitrogen containing heterocyclic compound such as ethyleneimine, pyrrole, pyrroline, piperidine, piperadine, morphorine and piperidone.

Examples of the tertiary amine include, for example, an aliphatic amine, such as triethylamine, tripropylamine and tri-n-butylamine; an aromatic amine such as N,N-dimethylaniline and N,N-diethylaniline; a cycloaliphatic amine such as N,N-dimethylcyclohexylamine; and a nitrogen-containing heterocyclic compound such as N-methyl ethyleneimine, N-methyl pyrrole, N-ethyl pyrroline, N-methyl piperidone and N-methyl piperidine.

Examples of the lactam are a lactam having 4 to 12 carbon atoms including, for example, γ-butyrolactam (pyrrolidone-2), δ-valerolactam (piperidone-2), γ-valerolactam (2-methyl pyrrolidone-5) and ε-caprolactam. Example of an N-alkyl derivative thereof include, for example, N-methyl pyrrolidone, N-ethyl pyrrolidone, N-isopropyl pyrrolidone and N-methyl caprolactam.

The acid amides are derived from an acid chloride of, for example, carboxylic, sulfonic, phosphoric or phosphonic acid and are represented by the following general formulae: carboxylic amide $R^4-(CONH_2)_n$, sulfonamide $R^5-SO_2 \cdot NH_2$, phosphor amide $PO(NH_2)_3$, phosphonous amide $R^6P(NH_2)_2$ and phosphone amide $R^7PO(NH_2)_2$, wherein $R^4$ is hydrogen or hydrocarbon having a $C_1-18$ alkyl, alkenyl, or aryl group which may be substituted with halogen, $n$ is 1 or 2 and each $R^5$, $R^6$ and $R^7$ represents an alkyl group having $C_1-18$ or aryl.

Examples of the compound represented by $R^4$—CO—$NH_2$ include, for example, formamide, acetamide, acrylamide, capronamide, caprinamide, stearamide, maloinamide, adipamide and benzamide; and examples of an N-alkyl derivative thereof include, for example, N,N-dimethylformamide, N-methylformamide, N,N-dimethylacetamide, N,N-dimethyltrichloroacetamide, N,N-dimethyl trimethylamide, and N-methyl acrylamide; the N,N-dimethylformamide/$AlCl_3$ complex in particular is superior in catalytic activity.

An example of an $R^5-SO_2-NH_2$ compound is P-toluene sulfonamide and a dialkyl derivative is exemplified as N,N-dimethyl-p-toluene sulfonamide.

Examples of a $PO(NH_2)_3$ compound are in particular $C_1 - C_8$ alkyl derivatives, for example, hexaalkyl phosphoramide, especially hexamethylphosphoric triamide, $(PO[N(CH_3)_2]_3)$. A complex of this compound with $AlCl_3$ is especially suitable for a polyoxazolidone foam catalyst as illustrated in the examples appearing hereinafter. This compound shows superior catalyst activity and, additionally, foam collapse is eliminated resulting in a foamed material containing a desirable cell structure.

A typical example of $R^6P(NH_2)$ type compound is $C_6H_5P(NH_2)_2$.

A typical example of $R^7PO(NH_2)_2$ type compound is $C_6H_5PO\ N(CH_3)_2\ _2$.

Compounds represented by the general formula of $R^1_3P$ include a phosphine compound having a hydrocarbon such as alkyl and cycloalkyl of 1–8 carbon atoms or aryl of 6–18 carbon atoms. Examples of these compounds include, for example, a primary phosphine, such as $PH_2(CH_3)$, $PH_2(C_2H_5)$ and $PH_2(C_6H_5)$ a secondary phosphine, such as $PH(C_2H_5)_2$ and $(C_2H_5)$. $P(H)C_2H_4P(H)(C_2H_5)$; and a tertiary phosphine such as $P(CH_3)_3$, $P(C_8H_{17})_3$, $P(CH_3)_2(C_6H_5)$ and $P(C_6H_5)_3$. Further, a heterocyclic tertiary phosphine may be used as represented by the following examples:

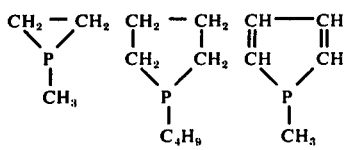

Examples of a complex of phosphine and a Lewis acid include, for example:
$TiCl_4 \cdot PH_2(CH_3)$, $ZnCl_2 \cdot PH_2(C_2H_5)$, $[Fe(PH_2C_6H_5)_4]Cl_2$, $[Fe(PH_2C_6H_5)_4]Br_2$, $ZnCl_2[PH(C_2H_5)_2]$, $FeCl_3[PH(C_2H_5)_2]$, $[CoCl_2(C_2H_5P(H)C_2H_4P(H)C_2H_5)]Cl$, $AlCl_3[P(CH_3)_3]_2$, $AlCl_3[P(C_8H_{17})_3]_2$, $TiCl_4P(CH_3)_3$, $ZnCl_2[P(CH_3)_3]_2$, $SnCl_4[P(CH_3)_3]_2$, $CoCl_2[P(C_2H_5)_3]_2$, $ZnI_2[P(CH_3)_2C_6H_5]_2$, $ZnCl_2[P(C_6H_5)_3]_2$ and $FeCl_3[P(C_6H_5)_3]_2$. The compounds represented by the general formula $R^3_3PO$ are, in general, a phosphoryl compound containing hydrocarbon such as alkyl, cycloalkyl, alkoxy or acyl having 1–8 carbon atoms or aryl having 6–18 carbon atoms. These hydrocarbons may be substituted by alkoxy, acyloxy or halogen. Examples thereof include:
$(C_2H_5)_3PO$, $(i-C_3H_7)_3PO$, $(C_4H_9)_3PO$, $(C_4H_9-CH(C_2H_5)-CH_2)_3PO$, $(C_6H_5)_3PO$, $(ClCH_2)_3PO$, $(CH_2Cl)_2(CH_3)PO$, $(CF_2=CF)_3PO$, $(CF_3)_2(CHF_2CF_2)PO$, $(C_4H_9O)_3PO$, $(C_6H_5)(C_2H_5O)_2PO$, $(C_2H_5)_2(C_6H_5CH_2CO)PO$, $(CH_3COOCH_2)_3PO$, $(C_4H_9OCH_2CH_2)_3PO$ and $(C_6H_5)_2P(O)C_2H_4P(O)(C_6H_5)_2$.

The compounds represented by the general formula of $R^3_2SO$ are, in general, a sulphoxide compound containing hydrocarbon such as alkyl and cycloalkyl having 1–8 carbon atoms, aryl or aralkyl having 6–18 carbon atoms. Preferred examples thereof include, $(CH_3)_2SO$, $(C_2H_5)_2SO$, $(C_3H_7)_2SO$, $(C_6H_5)_2SO$ and $(C_6H_5CH_2)_2SO$. These compounds are capable of forming a complex with a Lewis acid such as $AlCl_3OS(CH_3)_2$ and $ZnCl_2OS(C_3H_7)_2$.

The complex of a Lewis acid and a Lewis base which may be used as a catalyst according to this invention is conveniently prepared by mixing both compounds under agitation in the presence or absence of a solvent. These solvents include an aromatic hydrocarbon such as benzene and toluene; a ketone such as acetone; ether such as dioxane; and an ester such as methylcellosolve. The molar ratio of the Lewis base to the Lewis acid is generally 1 –50:1 but, in some cases, it is preferred to use as small a molar ratio as possible. For example, if a Lewis base has a tendency to cause foam collapse, the amount of the Lewis base is preferably reduced. When the oxazolidone compound is produced in a solvent, the above-mentioned problem is eliminated. For purchases of weighing and mixing, the preferred form of the complex is a solution. In this regard, the molar ratio range is preferably 3–20:1, especially 5–10:1. If a lower molar ratio is employed, the complex is conveniently prepared in one of the above-mentioned inert solvents.

Although, it is desirable to handle the complex in the form of a solution, the complex in a solid or a syrup is soluble in either an isocyanate compound or an epoxy compound which is the starting material of the oxazolidone compound according to this invention. Therefore, the complex acts as a homogeneous catalyst.

In the synthesis of an oxazolidone compound, the complex may be added directly to any of the starting materials, or, alternatively, the complex may be added to a mixture of the starting materials.

The isocyanate compound which is the starting material of oxazolidone compound may be any one of a variety of organic or inorganic compounds containing one or more isocyanate groups. Examples of such organic isocyanate compounds include, unmodified organic isocyanate including, for example, an organic monoisolyanate, such as methyl isocyanate, ethyl isocyanate, butyl isocyanate, phenyl isocyanate and p-tolyl isocyanate; an organic diisocyanate, such as tolylene diisocyanate, diphenylmethane diisocyanate, isophorone diisocyanate, xylene diisocyanate and 1,5-naphthylene diisocyanate; and a mixture of organic polyisocyanates such as polymethylene polyphenyl polyisocyanate and various modified organic isocyanates.

Examples of the modified organic isocyanate are various isocyanate group-containing compounds which are produced by reacting an active hydrogen-containing compound such as water, an alcohol, an amine, an amide and a carboxylic acid with a stoichiometrically excess amount of an organic polyisocyanate compound. For example, an organic polyisocyanate which contains an organic triisocyanate having a biuret structure and is produced by heating tolylene diisocyanate with a small amount of water, and an isocyanate-terminated urethane prepolymer which is produced by reacting tolylene diisocyanate with a polyether polyol.

An organic polyisocyanate having a carbodiimide group produced by heating an organic polyisocyanate is also used.

Further, other polyisocyanates, such as a reaction product of an organic dihalide and sodium cyanate may be used (refer to Japanese Patent Publication 7269/72). The resultant Product is a mixture of various isocyanates having isocyanurate ring.

A polyisocyante having an isocyanurate ring may also be used. This polyisocyanate is produced by partially trimerizing a polyisocyanate compound in the presence of a trimerization catalyst, for example, a tertiary amine such as 2,4,6-tris(dimethylaminomethyl) phenol and N,N-dimethyl piperazine.

Examples of the inorganic isocyanate compound include, for example, silicon tetraisocyanate, $Si(NCO)_4$, and various phosphorus polyisocyanate, such as $P(NCO)_3$, $PO(NCO)_3$ and $RP(NCO)_2$ wherein R is an organic group. Such isocyanate compounds may be used alone or in combination.

Among the abovementioned various isocyanate compounds, organic isocyanate compounds are preferred and especially aromatic isocyanate compounds.

The epoxy compound which may be used according to this invention is a compound having one or more oxyrane rings. Example of these compounds include, for example, a monoepoxy compound such as propylene oxide, 1,2-butene oxide, 2,3-butene oxide, styrene oxide, phenyl glycidyl ether and epichlorohydrine; a diepoxy compound such as glycidyl ether of bis-phenol A, vinyl cyclohexene dioxide and bis(3,4-epoxy-6-methyl cyclohexyl methyl)adipate; a polyepoxy compound such as a glycidyl ether of a novalak resin and of a polyhydric alcohol; and other various epoxy compounds such as a glycidyl derivative of a heterocyclic compound and of an aromatic primary amine and an epoxy derivative of an inorganic compound.

Embodiments of the polyepoxy compound have been disclosed in U.S. Pat. No. 3,817,938 and the following literature:

Epoxy Resins (American Chemical Society, 1970) by Henry Lee, Handbook of Epoxy Resins (McGraw Hill Book Co., 1967) by Henry Lee and K. Neville, Epoxy Resins Their application and Technology (McGraw Hill Book Co., 1957) by Henry Lee and K. Neville, Epoxy Resins Reinhold Publishing Corp., 1958) by I. Skeist, Ring-Opening Polymerization (Marcel Decker, 1969) by K. C. Frish and S. L. Reegan, Production and Application of Epoxy Resin (Kobunshi Kagaku Kankokai) by H. Kakiuchi, Epoxy Resin (Shokodo) by H. Kakiuchi and Epoxy Resin (Nikkan Kogyo Shinbunsha) by K. Hashimoto.

The reaction of an isocyanate compound and an epoxy compound according to this invention is carried out in the presence or absence of a solvent which may be a hydrocarbon such as benzene and toluene, a ketone such as methylcellosolve.

According to this invention, when a foamed material is produced by reacting an isocyanate compound and an epoxy compound together with a foaming agent, it is preferred to use aromatic compounds as both components in virtue of their high reaction rate. On the other hand, for a film and a coating material, an aliphatic isocyanate compound and an aliphatic epoxy compound are selected in order to produce a product having a reduced tendency to yellow or discolor.

The amount of the catalyst and the reaction conditions employed may vary within a wide range.

The reaction temperature is usually above room temperature, for example, from 40° to 200° C. The reaction time may vary depending upon, for example, the type and amount of the catalyst and the reaction temperature used. If the temperature is from 100° to 150° C then a reaction time of from one to five hours is recommended.

The amount of the catalyst may vary depending upon the activity of the catalyst and the reaction temperature. For example, when a polyoxazolidone foam is produced, a high reaction rate is required to permit the reaction to proceed at room temperature. This procedure results in the prevention of foam collapse and the formation of desirable cells. Therefore, a relatively large amount of the catalyst (in general, from 1 to 5% by weight based on the weight of the raw materials) is used.

On the other hand, when an isocyanate-terminated oxazolidone prepolymer and a polyoxazolidone suitable for coating are produced, it is not required to use a high reaction rate but the reaction mixture may be heated. Then, a relatively small amount of the catalyst (in general, from 0.001 to 15% by weight based on the weight of the raw materials) may be used.

When a polyoxazolidone compound is produced from an organic polyisocyanate and a polyepoxy compound, the equivalent ratio of both may vary widely and an appropriate choice may be made. For example, when an isocyanate-terminated polyoxazolidone is produced, the equivalent ratio of epoxy/NCO is usually from 0.1 to 0.9 and where an oxyrane ring-terminated polyoxazolidone is produced, the equivalent ratio of NCO/epoxy is usually from 0.1 to 0.9.

The polyoxazolidone produced according to this invention may be used for the production of various useful polymeric materials. For example, a polymeric material produced by reacting an organic diisocyanate compound and a diepoxy compound in an equivalent ratio of about one is used for paint, adhesive, resin and synthetic fibers.

A reaction product containing polyoxazolidone is produced with an equivalent ratio of NCO/epoxy greater than 1 and which contains a residual free isocyanate group. Thus, the reaction is continued by the addition of a trimerization catalyst of the isocyanate group, for example, a tertiary amine such as 2,4,6-tris(-dimethylaminomethyl) phenol. This results in a polymer having an isocyanurate ring and an oxazolidone ring which is suitable for use as a resin, elastomer, paint and adhesive and this polymer is foamed by a foaming agent such as trichloromonofluoromethane to produce a heat resistant foamed material.

Further, where a polyfunctional active hydrogen-containing compound such as a polyhydric alcohol, a polycarboxylic acid, a polyamine and a polyamide is added to the abovementioned product having polyoxazolidone, a polymer is produced having an oxazolidone ring an urethane linkage, an amide linkage, an urea linkage and an acyl urea linkage which may also be converted into a foam, resin, elastomer, paint or adhesive.

On the other hand, an oxyrane ring-terminated polyoxazolidone can result in a polymer if it is reacted with a conventional epoxy-curing agent such as an amine and an acid anhydride.

This invention will further be explained by the following examples which are for illustrative purposes only and are not meant to limit the present invention in any manner.

EXAMPLES 1 to 17

A mixture of 0.1 mole (11.9 g) of phenyl isocyanate, 0.1 mole (15.0 g) of phenylglycidyl ether, 50 ml of benzene, a complex catalyst (listed in Table 1) in an amount of from 5 to 10 millimoles was heated under reflux for 7 hours and allowed to stand over night. Then, the precipitated crystals were filtered off and the yield was calculated.

The yield and melting point of the product, 3-phenyl-5-phenoxymethyl-2-oxazolidone, are shown in Table 1.

The reactions proceeded homogenously throughout the process. Though the foregoing Examples show a reaction in a solvent to obtain a product of low molecular weight, the following Examples set forth reactions in the absence of any solvent to produce a uniform polymer. This is proof of the superiority of the homogeneous catalyst according to this invention.

Table 1

| Example No. | Catalyst Type | Amount (m.mole) | Yield (%) | Melting Point (° C) |
|---|---|---|---|---|
| 1 | AlCl₃.O⟨oxetane⟩ | 5 | 79.6 | 143 |
| 2 | " | 10 | 69.9 | 143 |
| 3 | AlBr₃.O⟨oxetane⟩ | 5 | 79.2 | 143 |
| 4 | AlI₃.O⟨oxetane⟩ | 5 | 68.8 | 143 |
| 5 | ZnCl₂.O⟨oxetane⟩ | 5 | 19.0 | 142 |
| 6 | ZnCl₂.O⟨oxetane⟩ | 10 | 33.5 | 142 |
| 7 | ZnBr₂.O⟨oxetane⟩ | 5 | 41.3 | 140 |
| 8 | FeCl₃.O⟨oxetane⟩ | 10 | 23.4 | 143 |
| 9 | AlCl₃.O⟨THP⟩ | 5 | 76.5 | 144 |

Table 1-continued

| Example No. | Catalyst Type | Amount (m.mole) | Yield (%) | Melting Point (° C) |
|---|---|---|---|---|
| 10 | AlCl₃.O(n-C₄H₉)₂ | 5 | 77.3 | 145 |
| 11 | AlCl₃.NH₂(n-C₄H₉) | 5 | 78.4 | 143 |
| 12 | AlCl₃.N(C₂H₅)₃ | 5 | 50.9 | 139 |
| 13 | AlCl₃.NMP*¹ | 5 | 85.5 | 143 |
| 14 | AlCl₃.HMPA*² | 5 | 63.9 | 143 |
| 15 | ZnBr₂.HMPA | 5 | 45.0 | 144 |
| 16 | AlCl₃.OP(CH₂—C(H)(C₄H₉)(C₂H₅))₃ | 5 | 90.7 | 144 |
| 17 | AlCl₃.OS(CH₃)₂ | 5 | 56.5 | 143 |

*¹ NMP: N-methyl pyrrolidone 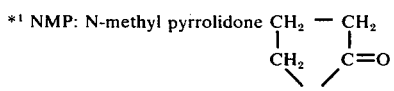

*² HMPA: Hexamethylphosphoric triamide 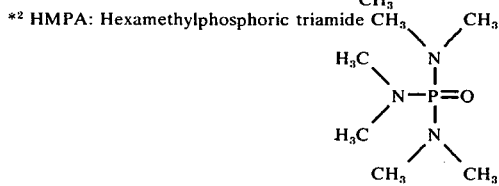

Among the catalyst complexes listed in Table 1, the catalytic activity of tris(2-ethyl hexyl) phosphineoxide-AlCl₃ complex was excellent, the product being precipitated at room temperature without heating.

EXAMPLE 18

Synthesis of polyoxazolidone 0.001 mole of zinc chloride-tetrahydorfuran complex was added to and dissolved in a mixture of 0.1 equivalent (14.4 g) of carbodiimide modified diphenylmethane diisocyanate (available from the Upjohn Co., Mich., as "Isonate 143L") and 0.1 equivalent (20 g) of bisphenol A epoxy resin (available from Shell Chemical Co., Japan as "Epikote 819"). The resulting solution was coated on an aluminum plate and heated at 70° C for 5 hours to obtain a clear, colorless coating.

The pencil hardness of the coating was 3H. The stream at a thermal gradient of 5° C/min. showed gradual thermal decomposition at 200° C, vigorous decomposition at about 350° C a weight loss of 50% at 370° C and a weight loss of 70% at 400° C. FIG. 1 shows TGA data and FIG. 2 shows IR Spectrum. In FIG. 2, a characteristic absorption of oxazolidone carbonyl at about 1720 cm⁻¹ is clearly shown.

EXAMPLE 19

A mixture of 0.1 equivalent (12.5 g) of 4,4'-diphenylmethane diisocyanate and 0.1 equivalent (20 g) of "Epikote 819" was mixed with 10 ml (0.005 mole) of a 10% solution of AlCl₃/n-C₄H₉- NH₂ complex in toluene with thorough agitation and the resulting mixture was coated on an aluminum plate and heated at 70° C for 6 hours to obtain a colorless, clear and hard film having a pencil hardness of 3H.

EXAMPLE 20

3.1g of AlCl₃. OS(CH₃)₂ as a catalyst was added to a mixture of 0.1 equivalent (12.5 g) of 4,4-diphenylmethane diisocyanate and 0.1 equivalent (18.8 g) of an epoxy resin of epichlorohydrinebisphenol A (available from Shell Chemical Co., Japan, under name of "Epikote 828" having a epoxy value of 189) and agitated thoroughly. Then, the resulting mixture was coated on a glass plate and heated at 70° C for 7 hours to obtain a colorless, clear and hard coating. The pencil hardness of the coating was 3H.

EXAMPLE 21

0.1 equivalent (8.7 g) of 80/20 TDI (tolylene diisocyanate, 2.4/2.6 being 80/20), 0.1 equivalent (7.0 g) of vinyl cyclohexene dioxide and 0.2 ml of a 36.8% solution of aluminum chloride in hexamethylphosphoric triamide were added to a 100 ml capacity beaper. After thorough agitation, the mixture was heated in an oven at 100 ° C for 3 hours to obtain a solid resin.

EXAMPLE 22

One liter flask, one equivalent (188 g) of "Epikote 838" which had been dried at 80° C under 0.3 mmHg, two equivalents (174 g) of 80/20 TDI and 0.36 g of $ZnCl_2 [P(CH_3)_3]_2$ were heated at 100° C in a one liter flask for 8 hours under a nitrogen stream to obtain oxazolidone containing 11.1% of a terminal isocyanate group.

The product can be used for producing a modified urethane coating.

EXAMPLE 23

Synthesis of urethane modified polyoxazolidone 0.02 equivalent (7.0 g) of polypropylene glycol having a molecular weight of 700 was added dropwise to 0.01 equivalent (14.4 g) of "Isonate 143L" to obtain an NCO-terminated urethane prepolymer. This prepolymer was mixed with 0.08 equivalent (16.0 g) of "Epikote 819" and 0.001 mole of zinc bromide/tetrahydrofuran complex, and the mixture was coated on an iron sheet and allowed to stand at room temperature for 24 hours to obtain a colorless and clear coating.

This coating had 2H pencil hardness and 50 cm/kg impact strength measured according to JIS (Japan Industrial Standard) K 5400.

The coating was subjected to the Eriehsen Test according to JLSZ 2247. There was no change of appearance of the coating was observed until the iron sheet was fractured.

The result of Spiral-Cut Test according to the procedures described in Journal of the Japan Society of Colour Material, Vol. 45, p. 22-28, 1972 was 50/50 showing excellent adhesion.

EXAMPLE 24

The production of polyoxazolidone foam 94.5 G (0.5 equivalent) of "Epikote 838", 2.0 g of a silicone surface active agent (available from Toray Silicone Co., Tokyo, Japan under name of "SH-193") and 15 g of trichloromonofluoromethane were mixed to prepare a premix. 67.5 g (0.5 equivalent) of polymethylene polyphenyl polyisocyanate (available from the Upjohn Co. under name of "PAPI 135" having an NCO equivalent of 134) and 6.1 g of a solution of a complex of $AlCl_3$hexamethylenephosphoric triamide (HMPA), ($AlCl_3$ being 36.8% and HMPA being 63.2% by weight), were added to this premix, and the mixture was immediately agitated vigorously to produce a foamed material. The cream time was 60 seconds, the rise time was 480 seconds and the resulting foam had a density of 40 kg/m³ with fine cell structure.

EXAMPLE 25

A mixture of one equivalent (134 g) of polymeric isocyanate (available from The Upjohn Co. under name of "Isonate 135" and having NCO equivalent of 134), 0.10 equivalent (20 g) of "Epikote 819" and 0.5 g of $ZnCl_2$/triethylamine complex was heated at 100° C for 2 hours to produce an isocyanate-terminated oxazolidone prepolymer. Than, 5.0 g of tris(2-chloroethyl) phosphate, 15.0 g of trichloromonofluoromethane, 1.0 g of a silicone surfactant (available from Union Carbide Corporation, N.Y., under name of "L-5340") and 5.0 g of 2,4,6-tris(dimethylaminoethyl) phenol were added to 100 g of the prepolymer under vigorous agitation to allow foaming whereby producing a poly-(oxazolidone-isocyanurate) foam was produced. The cream time was 7 seconds and the rise time was 60 seconds. The foamed material was cured at 80° C for 2 days and the resulting material was examined.

The foam density was 0.038 g/cm³ and the weight loss in a friability test according to ASTM C-421 was 17%.

EXAMPLE 26

10 g of glycerine propylene oxide polyether polyol (molecular weight of 300), 5.0 g of tris(2-chloroethyl)-phosphate, 15.0 g of trichloromonofluoromethane, 1.0 g of a silicone surfactant ("L-5340") and 5.0 g of 2,4,6-tris(dimethylaminomethyl) phenol were added to 100 g of the oxazolidone prepolymer produced in Example 25. The mixture was vigorously agitated to permit foaming to obtain a poly(oxazolidone-urethane-isocyanurate)foam. The cream time was 8 seconds, the rise time was 57 seconds and the foam density was 0.037 g/cm³.

EXAMPLE 27

One equivalent (134 g) of "Isonate 135", 0.1 equivalent (20 g) of "Epikote 828" and 2.0 g (0.005 mole) of an adduct of aluminum chloride and tris(2-ethylhexyl)-phosphineoxide were mixed and heated at 80° C for 2 hours to obtain an isocyanate-terminated oxazolidone prepolymer. Then, 5.0 g of tris(2-chloroethyl) phosphate, 15.0 g of trichloromonofluoromethane, 1.0 g of silicone surfactant ("L-5340") and 10 g of 2,4,6-tris-(dimethylaminomethyl)phenol were added to 100 g of the prepolymer under vigorous agitation to obtain a poly(oxazolidone-isocyanurate) foam.

The cream time was 13 seconds, the rise time was 70 seconds and the foam density was 0.038 g/cm³.

EXAMPLE 28

10 g of polyether polyol of glycerine-propyleneoxide adduct (molecular weight: 300), 5.0 g of tris(2-chloroethyl)phosphate, 15.0 g of trichloromonofluoromethane, 1.0 g of silicone surfactant ("L-5340") and 5.0 g of 2,4,6-tris(dimethylaminomethyl)phenol were added to 100 g of the oxazolidone prepolymer obtained in Example 27 under vigorous agitation to permit foaming whereby a poly(oxazolidone-urethane-isocyanurate) foam were produced. The cream time was 9 seconds, the rise time was 61 seconds and the foam density was 0.037 g/cm³.

What is claimed is:

1. A process for the production of a compound having an oxazolidone ring comprising reacting an isocyanate compound and epoxy compound in the presence of a catalyst of a complex of an aluminum halide with at least one Lewis base selected from the group consisting of an ether, a thioether, an amine, a lactam, an N-alkyl lactam, an amide, an N-alkyl amide, a phoshorus compound represented by formulae (1) ad (2) and a sulfur compound represented by formula (3):
1. $R^1_3P$, wherein each $R^1$ may be the same or different and repesents hydrogen and hydrocarbon with the proviso that all are not hydrogen at the same time, and when two or more are hydrocarbons they may be combined to form alkylene,
2. $R^2_3PO$, wherein each $R^2$ may be the same or different and represents an alkyl, cycloalkyl, aryl, alkoxy, or acyl group which may be substituted with an alkoxy, an acyloxy or a halogen group, and
3. $R^3_2SO$, wherein each $R^3$ may be the same or different and represents a hydrocarbon.

2. The process according to claim 1, wherein said Lewis acid is selected from the group consisting of $AlCl_3$, $AlBr_3$ or $ALI_3$.

3. The process according to claim 1, wherein said ether is an aliphatic or a cycloaliphatic ether containing 1 to 8 carbon atoms.

4. The process according to claim 1, wherein said amine is a primary, secondary or tertiary aliphatic amine containing 1 to 18 carbon atoms.

5. The process according to claim 1, wherein said lactam is N-alkyl lactam having a lactam moiety containing 4 to 12 carbon atoms.

6. The process according to claim 1, wherein said N-alkyl amide is a hexaalkylphosphoramide having an alkyl group of 1 to 8 carbon atoms.

7. The process according to claim 1, wherein said phosphorous compound is a tertiary phosphine 8. Thre process according to claim 1, wherein said phosphorus compound is a trialkyl phosphinoxide having an alkyl group of 1 to 8 carbon atoms.

9. The process according to claim 1, wherein said sulfur compound is a dialkyl sulfoxide having an alkyl group of 1 to 8 carbon atoms.

10. The process according to claim 1, wherein said isocyanate compound is an organic polyisocyanate compound and said epoxy compound is a polyepoxy compound.

11. The process according to claim 1, wherein said isocyanate compound is an aromatic monoisocyanate compound and said epoxy compound is a monoepoxy compound.

12. The process according to claim 1, wherein said catalyst is used in an amount of from 0.001 to 15% be weight based on the weight of said isocyanate and said epoxy compounds.

13. The process according to claim 1, wherein said isocyanate compound and said epoxy compound are reacted such at that the equivalent ratio of NCO/epoxide is from 0.1 to 10.

14. A process for the production of a compound having an oxazolidone ring comprising reacting an organic diisocyanate compound and a diepoxy compound in the presence of a catalyst of a complex of aluninum halide with at least one Lewis base selected from the group consisting of an ether, an amine, an N-alkyl lactam, an N-alkyl phosphoramide, phosphourous compounds represented by formulae (1) and (2) and a sulfur compound represented by formula (3):
1. $R^1_3P$, wherein each $R^1$ may be the same or different and represents hydrogen and hydrocarbon with the proviso that all are not hydrogen at the same time, and when two or more are hydrocarbons they may be combined to form alkylene,
2. $R^2_3PO$, wherein each $R^2$ may be the same or different and represents an alkyl, cycloalkyl, aryl, alkoxy or acyl group which may be substituted with an alkoxy, an acyloxy or a halogen group, and
3. $R^3_2SO$, wherein each $R^3$ may be the same or different and repesents a hydrocarbon, the amount of said catalyst being 0.001 to 15% by weight based on the weight of said diisocyanate and diepoxy compounds.

15. The process according to claim 14, wherein said catalyst is a complex of an aluminum halide selected from the group consisting of $AL CL_3$, and $ALBr_3$ and $AL I_3$ with a Lewis base selected from the group consisting of an aliphatic and cycloaliphatic ether having 1 to 8 carbon atoms, an aliphatic amine having 1 to 18 carbon atoms, and N-alkyl lactam having 4 to 12 carbon atoms, a hexaalkyl phosphoramide having an alkyl group of 1 to 8 carbon atoms, a trialkyl phosphinoxide having an alkyl group of 1 to 8 carbon atoms and a dialkyl sulfoxide having an alkyl group of 1 to 8 carbon atoms.

16. The process according to claim 14, wherein said Lewis base is selected from the group consisting of tetrahydrofuran, triethylamine, N-methyl pyrrolidone, hexamethylphosphoric triamide, tris (2-ethylhexyl) phosphinoxide or dimethyl sulfoxide.

17. The process according to claim 14, wherein said catalyst is complex of $AlCl_3$ and tris (2-ethylhexyl) phosphinoxide.

18. The process according to claim 14, wherein said catalyst is complex of a $AlCl_{L3}$ and N-methyl pyrrolidone.

19. The process according to claim 14 wherein said catalyst is complex of $AL C L_3$ and tetrahydrofuran.

20. The process according to claim 14, wherein said reaction is carried out in the presence of a foaming agent.

21. The process according to claim 14, wherein said catalyst is a complex of $AL C L_3$ and hexamethylphosphoric triamide.

22. The process according to claim 14, wherein said catalyst is used in an amount of from 1 to 5% by weight based on the weight of said dissocyanate and diepoxy compounds.

23. The process according to claim 14, wherein said organic diisocyanate compound and said diepoxy compound are reacted such that the equivalent ratio of NCO/epoxide is from 0.1 to 10.

24. The process according to claim 14, wherein said organic diisocyanate compound and said diepoxy compound are reacted such that the equivalent ration of NCO/epoxide is greater than 1 and in the presence of a foaming agent and a catalyst for trimerization of isocyanate.

25. The process according to claim 24, wherein said catalyst complex consists essentially of $AL C I_3$ and hexamethylphosphoric triamide.

26. The process according to claim 14, wherein said organic diisocyanate compound is an aromatic diisocyanate compound.

27. The process according to claim 14, wherein said organic diisocyanate compound is an isocyanate-terminated urethane prepolymer produced by reacting an aromatic diisocyanate compound and a polyhydroxy compound such that the equivalent ratio of NCO/OH is greater than 1.

* * * * *

UNITED STATES PATENT OFFICE
CERTIFICATE OF CORRECTION

PATENT NO. : 4022721
DATED : May 10, 1977
INVENTOR(S) : Kaneyoshi Ashida

It is certified that error appears in the above-identified patent and that said Letters Patent are hereby corrected as shown below:

Abstract, line 6, cancel "select" insert --selected--
Column 2, lines 2-4, cancel ".The...Al" insert --and iron family of the Periodic Table. The more preferred metals are Zn, Al and Fe, especially Al.
Column 2, line 48 cancel ";" insert --,--
Column 2, line 49 cancel "," insert --;--
Column 6, line 41 after "15%" insert --, preferably 0.01 to 10%,--
Column 7, cancel line 8 insert --done ring, a urethane linkage, an amide linkage, a--
Column 10, line 17 cancel "producing"
Column 11, line 21 cancel "or" insert --and--
Column 11, line 32 cancel "amide" insert --phosphoramide--
Column 12, line 14 cancel "and" first occurrence
Column 12, line 18 cancel "and" insert --an--
Column 12, line 28 cancel "or" insert --and--

Signed and Sealed this

Sixth Day of September 1977

[SEAL]

Attest:

RUTH C. MASON
Attesting Officer

LUTRELLE F. PARKER
Acting Commissioner of Patents and Trademarks